United States Patent [19]

Cumming

[11] Patent Number: 4,846,833
[45] Date of Patent: Jul. 11, 1989

[54] SEALED FRESNEL INTRAOCULAR LENS

[76] Inventor: J. S. Cumming, 1211 W. La Palma Ave., Suite 201, Anaheim, Calif. 92801

[21] Appl. No.: 198,572

[22] Filed: May 25, 1988

[51] Int. Cl.⁴ .............................................. A61F 2/16
[52] U.S. Cl. ......................................................... 623/6
[58] Field of Search ............................................ 623/6

[56] References Cited

U.S. PATENT DOCUMENTS

Re. 31,998 10/1985 Myers ...................................... 623/6
4,661,108 4/1987 Grendahl et al. ....................... 623/6
4,673,406 6/1987 Schlegel ................................. 623/6

FOREIGN PATENT DOCUMENTS 2180160A 3/1987 United Kingdom .................... 623/6

Primary Examiner—Ronald L. Frinks
Attorney, Agent, or Firm—Keith D. Beecher

[57] ABSTRACT

An intraocular lens of the Fresnel type which is constructed so that the Fresnel surface itself is sealed by the posterior capsule surface to overcome the problems encountered in prior intraocular lenses in which the Fresnel surface is exposed. The Fresnel lens surface is recessed entirely within the posterior surface of the intraocular lens in an open recess to form a space between the posterior face and posterior capsule surface when the intraocular lens is positioned in the eye. The sealed space facilitates the use of a YAG laser for a posterior capsulotomy should posterior capsule opacification occur.

3 Claims, 2 Drawing Sheets

SEALED FRESNEL INTRAOCULAR LENS

BACKGROUND OF THE INVENTION

When the material within the lens capsule of the eye becomes clouded a cataracteous condition results thereby obstructing the passage of light. Two forms of surgery are presently used to correct this condition.

The first form of surgery is known as intracapsular cataract extraction by which the lens and entire capsule are removed intact. In order to accomplish this, the surgeon pulls the lens free from the zonules or suspensory ligaments which normally engage the periphery of the capsule. The entire lens and capsule with its content material intact are then removed.

The second form of surgery is known as extracapsular cataract extraction, which involves making an incision through the anterior surface of the lens capsule. The clouded cellular material of the lens is then removed through the incision by suction of phacoemulsification, without removing the entire capsule. The clear rear wall of the capsule, known as the posterior capsule surface, remains in place in the eye. The zonules and the peripheral portions of the anterior capsule surface, which are known as the anterior capsule flaps, also remain in place.

The trend in cataract surgery has been towards the latter or the extracapsular procedure, because of certain undesirable complications which may result from intracapsular surgery.

Both the intracapsular and extracapsular cataract extraction procedures eliminate the light blockage due to the cataract. However, the light that now enters the eye through the cornea and pupil is unfocused due to the removal of the natural lens of the eye. Focusing may be achieved by positioning a contact lens on the external surface of the cornea to the eye, and/or by the use of spectacles. Although such external lenses are generally satisfactory, there are disadvantages because when they are removed the patient effectively has virtually no sight. The preferred alternative is to implant an artificial intraocular lens (IOL) directly into the eye.

The entire area behind the lens is normally filled with a jelly-like material called the vitreous humor. Occasionally during intracapsular surgery, when the lens is removed intact, the vitreous humor comes up through the pupil and it may escape from the eye through the incision that was made in order to carry out the intracapsular extraction. This gives rise to adverse side effects.

Cystoid Macular Edema (CME) is another complication which occurs more frequently in intracapsular surgery. This is a swelling of the macula of the retina. It is believed that the swelling is caused by certain enzymes which are released from the iris and migrate through the vitreous humor and back to the macula. This is a serious complication. During extracapsular surgery, however, since the posterior capsule remains intact, the vitreous humor is prevented from getting into the anterior chamber of the eye. The incidence of cystoid macular edema or retinal detachment is markedly reduced with extracapsular surgery.

Accordingly, from the viewpoint of reducing postsurgical complications, extracapsular extraction is the presently preferred surgical procedure. The present invention provides an improved intraocular lens which is particularly advantageous for use in conjunction with extracapsular extractions. It can also be used in intracapsular extraction when place in the anterior chamber.

Harold Ridley was the first physician in the early 1950's to implant a posterior chamber lens into the eye. Ridley used a biconvex lens which was about the same shape, but was approximately 1 millimeter smaller in diameter than the human lens. The Ridley lens had a weight in air of 112 mg and, accordingly, represented an extremely heavy object to be implanted into the eye.

The usual prior art intraocular lens is rigid and is formed, for example, of an appropriate transparent plastic such as methyl methacrylate. However, U.S. Pat. No. 4,573,998 discloses an intraocular lens structure which comprises a deformable optical zone portion with prescribed memory characteristics. The optical zone portion of the lens described in the patent, may be deformed by rolling or folding to reduce the diameter of the optical zone so that the lens may be inserted into the eye through a relatively small incision, as compared with the incision required for the insertion of the rigid lenses. After insertion into the eye, the optical zone portion of the lens returns to its original configuration. The deformable lens described in the patent maybe formed to have its optical zone composed of one or more suitable flexible materials such as polyurethane elastomer, silicone elastomer, hydrogel polymer collagen compounds, organic or synthetic gel compounds and combinations thereof.

The use of a deformable intraocular lens during the surgical procedure has distinct advantages over the rigid intraocular lens, because the latter requires a relatively large incision in the ocular tissue. This leads to a relatively high complication rate, such as astigmatism, vitreous loss, retinal detachment, and cystoid macular edema. Accordingly, these disadvantages are overcome to a large extent by the use of the lens disclosed in the patent which requires a smaller incision for its insertion into the eye. The small incision also facilitates rapid physical and visual rehabilitation.

The lens of the present invention may be flexible, and it may be formed of any of the materials listed above. However, the lens of the present invention when made of flexible material represents a distinct advantage over the lens described in U.S. Pat. No. 4,573,998, in that it can be deformed into a much smaller diameter for insertion into the eye. Accordingly, the incision required for the insertion of the lens of the present invention is so small that suturing of the incision may not be required at the completion of the operation. Therefore there should be virtually no surgically induced astigmation.

The lens described in U.S. Pat. No. 4,573,998, like the human lens has biconvex configuration. This means that it must have a significant thickness in order to perform the required focusing function.

Another type of lens which overcomes many of the biconvex lens shortcomings, i.e. thickness, folding difficulties, longer incisions required, is the Fresnel lens, whose application to intraocular lenses is described in U.S. Pat. No. 4,673,406. Such a lens can be made sufficiently thin so that it may be inserted through a very small incision and if made of the appropriate material may unfold to its original shape after insertion.

Fresnel optics with the opposite side spherical are generally stiffer, as one might expect, and therefore resist bending or folding and generally require a larger incision for insertion. The combination of Fresnel surfaces on the front and back side has proven self-defeating in other applications. Therefore, it may be assumed that the same would happen in the case of a two sided Fresnel optic, i.e. a Moire Pattern is formed. In other words, interference of the light is caused by the superimposition of two regularly spaced patterns, causing light and dark rings.

The open Fresnel lens has further shortcomings which relate primarily to the medical aspects of such devices. Since the Fresnel surface may be placed in the sulcus of the eye or the capsular bag, the Fresnel surface is adjacent to the iris. The diameter of the iris, which is a variable opening in the eye, changes rapidaly as the ambient illumination changes. Under bright daylight conditions, the iris opening may be only a few millimeters, changing to wide open under darkened conditions. The action is entirely involuntary. The Fresnel surface in order to be effective must have sharp ridges at the juncture of individual lenticules. These, of course, could abrade the rear surface of the iris, causing inflammation. Also particulate pigment sheared from the iris or inflammatory cells may lodge in the grooves of the Fresnel, destroying its effectiveness.

The lens of the present invention overcomes the foregoing objections to a Fresnel lens plus adds some unique features not present in existing intraocular lenses of any type.

The lens of the present invention utilizes a Fresnel surface sealed from its immediate environment. Fresnel lenses are flat optical devices which focus light from a series of concentric grooves or lenticules which are molded or cut into a surface of the device. Each groove is trapezoidal in crosssection, with the face angles varied in a controlled manner at different distances from the optical axis of the lens. Specifically, the Fresnel elements are formed on one surface of the optical zone of the lens, and no large thickness is required. This is because the Fresnel elements perform the desired focusing action by acting as a series of concentric prisms, deviating the incoming light rays to a common point. This means that the lens of the prior invention, when made of flexible material, may be folded, rolled or otherwise deformed to an extremely small diameter for insertion into the eye through an extremely small incision.

Specifically, the lens of this invention has one flat or plano side, rather than being biconvex, because light is focused by means of a series of concentric grooves cut or molded into a surface of the lens, in accordance with Fresnel lens principles. Each groove formed in the surface of the lens is trapezoidal in cross-section, with the face angles of the successive grooves being varied in a controlled manner as a function of the distances of the respective grooves from the optical axis of the device.

Through computer controlled machinery, Fresnel lenses may be provided which are corrected for spherical aberration, reduce scatter and improve focusing efficiency. The combination of the sealed Fresnel surface on one side of the lens, with a flat plano surface or spherical surface on the opposite side, allows the intraocular lens of the invention to constitute an excellent replacement for the natural lens.

The sealed Fresnel surface can be applied to all materials with optical properties, including HEMA (hydrooxyethylmethylmetharylate). This is a hydrophilic material from which soft contact lenses are currently manufactured. The sealed Fresnel principle can be applied to the HEMA<in its dehydrated state or after hydration. The lens may then be inserted into the eye in a dry, shrunken, small state or after hydration by deforming the surface.

The sealed Fresnel surface reduces reflection as compared to a conventional biconvex lens or plano convex lens, and there is less dispersion with the Fresnel surface lens. The Fresnel lenticules can be arranged to reduce spherical aberration.

The sealed Fresnel principle can be applied to all lens materials that are inserted inside the eye, including hard materials and heat sensitive hard materials that can be deformed and fixed outside the eye and which resume an optical shape after insertion into the eye, the heat of the aqueous causing them to open and flatten.

However, there are certain problems which arise with respect to the Fresnel intraocular lens. For example, in order for the Fresnel lens to function properly it must have sharply shaped lenticules which often become a source of irritation when drawn across the surface of the iris. Frequently, the body's response to such irritation is to grow new tissue over the source of the irritation. This action ultimately destroys, or at least seriously reduces the effectiveness of the lens.

Another problem which arises is that the aqueous humor of the eye frequently contains particles which tend to lodge in the grooves of the Fresnel lens; and which tend to destroy the Fresnel surface or at least adversely affect its optical efficiency.

Accordingly, an object of the present invention is to provide a Fresnel type intraocular lens which has all the advantages of the prior art lenses but which is constructed so that the Fresnel surface itself is sealed to overcome the problems encountered by the prior art lenses.

DETAILED DESCRIPTION OF THE ILLUSTRATED EMBODIMENT

Figure 1:
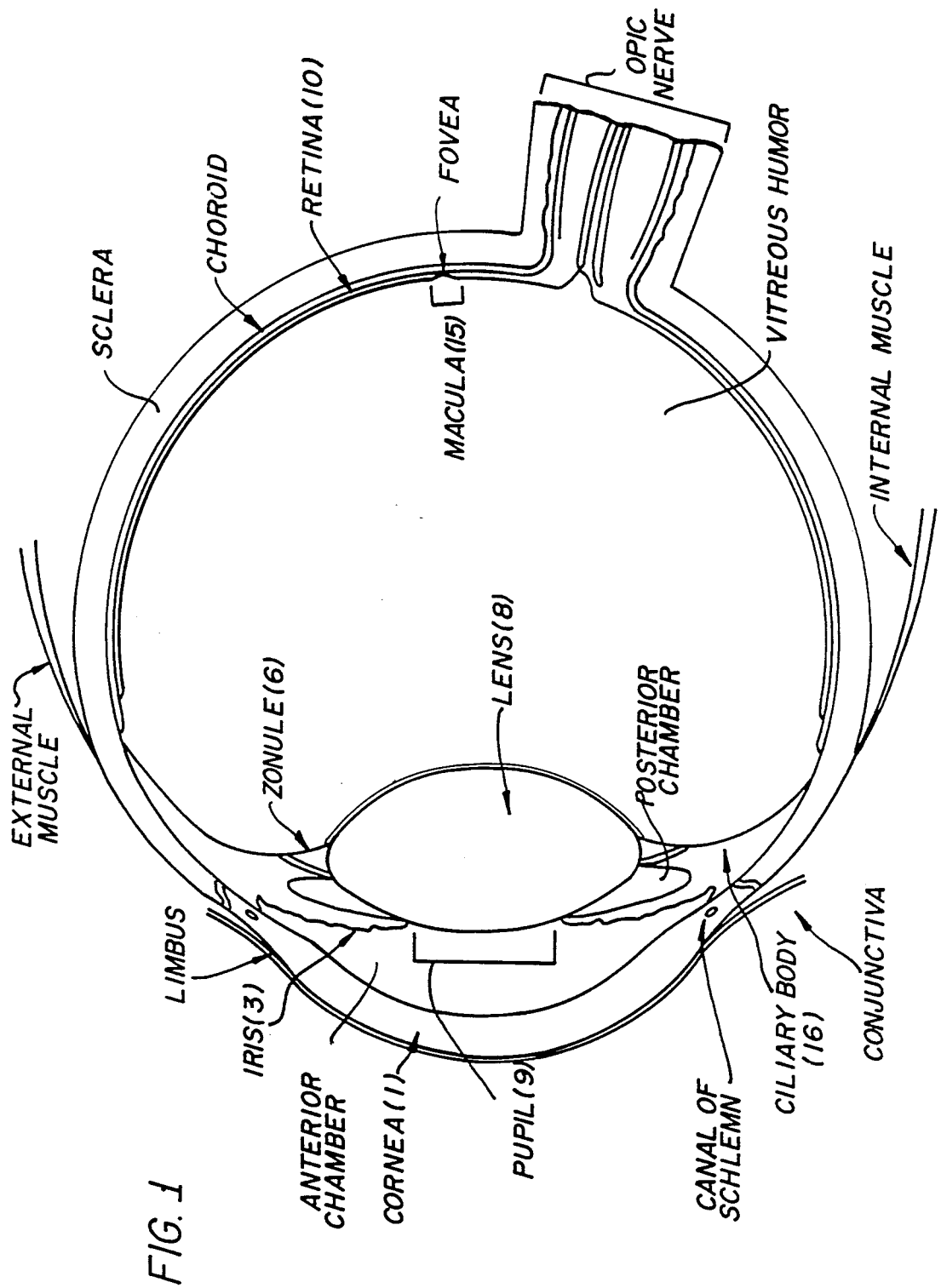
FIG. 1 is a cross-sectional view of a typical human eye.

As shown in FIG. 1, the human lens 8 of the eye is situated behind the pupil 9 and iris 2, and it functions to focus light that has passed through the cornea 1 and pupil 9 onto the retina 10 at the rear of the eye. The lens 8 is a transparent structure formed of thin curved rod-shaped ectodermal cells. The lens 8 is biconvex and is surrounded by a thin transparent capsule. Zonules 6 support the lens capsule at its periphery by suspensory ligaments which are part of the ciliary body 16. The contraction of the ciliary body relaxes the zonules, allowing the lens to become more spherical thereby altering its focal length.

Because of its large diameter and weight, the Ridley lens exerted undue pressure on the ciliary body 16 of FIGURE 1. The ciliary body is the annular structure on the inner surface of the eye surrounding the lens 8 and including the ciliary muscle to which the zonules 6 are connected. Other adverse side effects also occurred from the use of the Ridley lens, including Glaucoma. In some instances, the Ridley lens became loose and sank to the back of the eye. There were also cases in which the Ridley lens shifted downwardly so that its axis was no longer centered with respect to the pupil. For the foregoing reasons, the Ridley lens was soon abandoned.

However, even through the Ridley lens was abandoned, the Technology continued and countless cataract surgeries are now performed annularly through the world using intraocular lenses.

Intraocular lenses generally fall into two major classes, anterior chamber lenses and posterior chamber lenses. Anterior chamber lenses are positioned in the anterior chamber 2 (FIG. 1) in front of the iris 3; whereas posterior chamber intraocular lenses are positioned behind the iris and may be mounted within the bag composed of the anterior capsule flaps and posterior capsule surface which remains in place after extracapsular surgery. The lens 50 of the present invention is intended to be placed in the posterior chamber as shown in FIG. 2.

Figure 3:
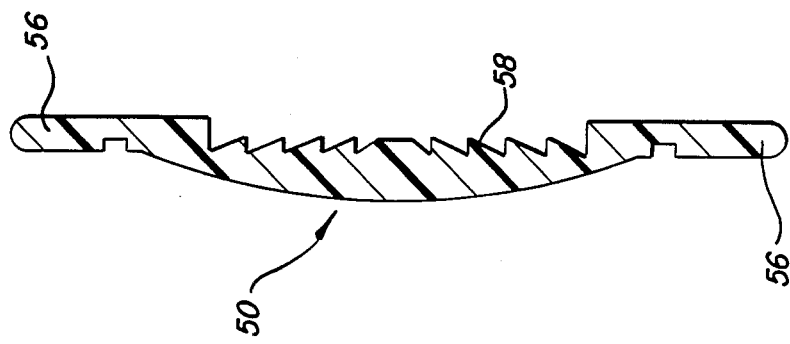
FIG. 3 is a section of the intraocular lens of FIG. 2, on a somewhat enlarged scale.
Figure 2:
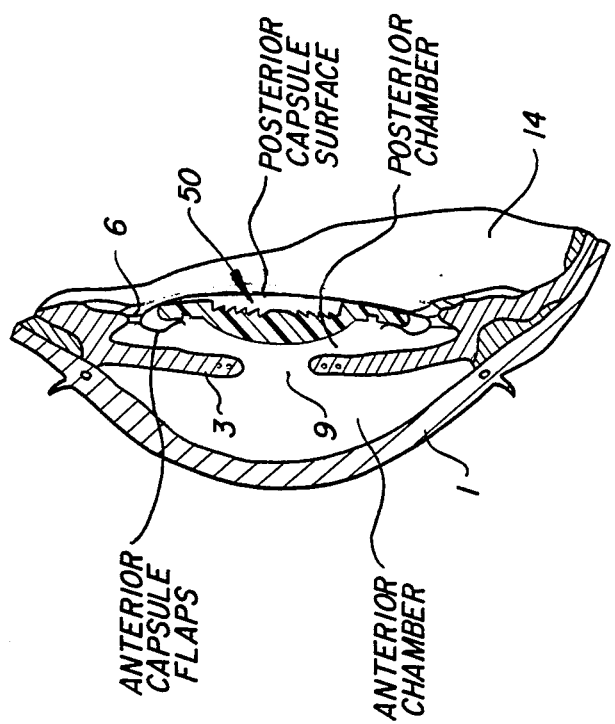
FIG. 2 is a cross-sectional view of the eye with a lens embodying the invention in place.

The intraocular lens 50 shown in FIGS. 2 and 3 is intended to replace the human lens 8 of FIG. 1 by means of the cataract surgical procedure described above. The lens is held in place in the eye by appropriate haptic portions 56.

The intraocular lens 50 in accordance with the present invention, and as best shown in FIG. 2, preferably has a convex anterior surface and it has a Fresnel lens formed on its posterior surface. In accordance with the present invention the Fresnel lens is recessed with respect to the plane of the haptics portion 56 of the lens. This provides a space 58 between the Fresnel lens and the posterior capsule surface, as shown in FIG. 3.

The convex anterior surface of the lens 50 gives stability to the Fresnel lens and also serves to assist in the refraction of the light through the lens. However, the anterior surface may be flat, if so desired.

The convex anterior surface of the lens allows for different optical powers to be achieved while maintaining the flat Fresnel lens on the posterior side of the lens. The convex surface may be made of different thicknesses and curvatures to provide different lens powers, focal distances and desired optical corrections. Conversely, the power of the anterior surface may remain constant and different lens powers may be produced by changing the power of the posterior Fresnel surface.

The lens 56 may be made flexible if so desired so that it may be deformed into an extremely small diameter for insertion into the eye through an extremely small incision.

The Fresnel lens, as described above, is countersunk or recessed entirely into the posterior face of the lens in an open recess with space 58 being defined between the posterior capsule surface and the Fresnel surface. This posterior space 58 facilitates the use of a YAG laser for posterior capsulotomy which serves to treat posterior lens opacification (clouding). This operation is sometimes necessary when the posterior capsule surface becomes cloudy. If the posterior side of the lens were not displaced from the posterior capsule surface, the focusing of the laser beam to cut a hole in the posterior capsule surface has a tendency to damage the lens.

The recessed Fresnel lens configuration also has an advantage in that it enables the posterior capsule surface to seal the Fresnel lens from deposits which serve to reduce the resolution of the lens should they become lodged in the Fresnel surface. With the capsulorhexis or circular capsulstomy technique of anterior capsulstomy, the posterior lens capsule is pulled tight, like a drum head across the posterior surface of the lens. This forms a seal protecting the Fresnel surface.

The invention provides, therefore, an improved intraocular lens which utilizes Fresnel principles to achieve superior surgical results as compared with other intraocular lenses. The lens when formed of flexible material may be deformed into an extremely small diameter for insertion into the eye through an extremely small incision.

The invention also provides a Fresnel intraocular lens that allows a constant Fresnel surface optical power and variable opposite surface optical power to determine the total power of the lensor vice versa. When formed of flexible material, the intraocular lens has prescribed memory characteristics, with a recessed Fresnel flat surface on one side of the lens, so that it may be deformed or rolled into a very small configuration for insertion through a smaller incision into the eye than was before possible.

The haptics may be made of the same material as the lens, or other materials such as Prolene (polypropylene) or other inert nonabsorbable plastics. The haptics are designed to hold the lens in place in the remanants of the capsular bag in the posterior chamber of the eye.

Specifically, the invention provides, an intraocular lens having recessed Fresnel lens elements formed on its posterior surface, with its anterior surface being convex or flat. The lens may be thinner than the prior art flexible intraocular lenses presently being implanted into the eye, and it may be folded or rolled to be inserted through a smaller incision in the ocular tissue than the incisions presently required for the insertions of the prior art flexible introocular lens. The refracting surface of the lens is inherently thin since it is in the form of a Fresnel lens. The recessed Fresnel lens enables the posterior capsule surface to protect the Fresnel elements from deposits of debris which would otherwise reduce their optical properties. Also, the recessed Fresnel lens in the structure of the present invention facilitates the use of the Y.A.G. laser to pierce the posterior capsule surface without damaging the lens.

It will be appreciated that while a particular embodiment of the invention has been shown and described, modifications may be made. It is intended in the claims to cover all modifications which come within the spirit and scope of the invention.

I claim:

1. An intraocular lens for extracapsular cataract extraction to be positioned in the eye adjacent to the posterior capsule surface and which is configured to provide a space between the posterior face of the lens and the posterior capsule surface to facilitate laser piercing of the posterior capsule surface with the lens in place, and which inculdes a Fresnel lens formed on said posterior face and recessed entirely into said face in an open recess to form said space, whereby the Fresnel lens is sealed and protected by said posterior capsule when said intraocular lens is positioned in the eye.

2. The intraocular lens defined in claim 1, in which the anterior face of said lens has a convex configuration.

3. The intraocular lens defined in claim 1, in which the lens is formed of a flexible material.

* * * * *